United States Patent
Bessman et al.

(10) Patent No.: US 10,539,544 B2
(45) Date of Patent: Jan. 21, 2020

(54) HANDHELD TESTING DEVICE OF NITROGEN OXIDE SENSOR

(71) Applicant: PACCAR Inc, Bellevue, WA (US)

(72) Inventors: John Bessman, Mount Vernon, WA (US); Richard Jeffrey Currie, Mount Vernon, WA (US); Michael Gerty, Bellingham, WA (US); Nick Hertlein, Bellingham, WA (US)

(73) Assignee: PACCAR Inc, Bellevue, WA (US)

( * ) Notice: Subject to any disclaimer, the term of this patent is extended or adjusted under 35 U.S.C. 154(b) by 992 days.

(21) Appl. No.: 14/938,054

(22) Filed: Nov. 11, 2015

(65) Prior Publication Data
US 2017/0131251 A1    May 11, 2017

(51) Int. Cl.
*G01N 33/00* (2006.01)

(52) U.S. Cl.
CPC ....... *G01N 33/007* (2013.01); *G01N 33/0037* (2013.01)

(58) Field of Classification Search
CPC .................................... G01N 33/007
See application file for complete search history.

(56) References Cited

U.S. PATENT DOCUMENTS

| | | | | |
|---|---|---|---|---|
| 2010/0257846 A1* | 10/2010 | Weber | ................... | B01D 53/30 60/286 |
| 2014/0318216 A1* | 10/2014 | Singh | ................... | G01M 15/102 73/23.31 |
| 2016/0209383 A1* | 7/2016 | Gong | ................... | G01N 33/0037 |

* cited by examiner

*Primary Examiner* — Lisa M Caputo
*Assistant Examiner* — Alex T Devito
(74) *Attorney, Agent, or Firm* — Merchant & Gould P.C.

(57) ABSTRACT

A testing device is capable of testing a NOx sensor in an environment that does not have dew point detection capability. The testing device includes a connector configured to be coupled to the NOx sensor, an output indicator, and circuitry. The circuitry is configured to send an unverified dew point signal to the NOx sensor via the connector and receive a sensor signal from the NOx sensor via the connector. The unverified dew point signal includes an indication that a temperature of the environment is at or above the dew point. The sensor signal includes an indication of operation of the NOx sensor in the environment. The circuitry is further configured to determine a status of the NOx sensor based on the received sensor signal and indicate, via the output indicator, the status of the NOx sensor.

20 Claims, 6 Drawing Sheets

HANDHELD TESTING DEVICE OF NITROGEN OXIDE SENSOR

BACKGROUND

Nitrogen oxide (NOx) sensors are used to measure NOx levels in tailpipe emissions. In particular, NOx sensors are used in exhaust systems of modern diesel and lean-burn petrol engines to monitor tailpipe emissions. In a vehicle, a NOx sensor is typically coupled to a controller area network (CAN) to receive information from other sensors about the operating conditions of the vehicle. The NOx sensor measures NOx levels in tailpipe emissions based on the information about the operating conditions of the vehicle from the other sensors via the CAN.

One difficulty with NOx sensors is testing the NOx sensors, particularly in vehicle repair facilities. Traditionally, testing a NOx sensor in a vehicle includes running the vehicle for a time until the vehicle reaches a stable operating condition and then reading the NOx sensor output via a diagnostic connection of the vehicle's CAN. This allows the NOx sensor to receive information about the operating conditions of the vehicle from the other sensors via the CAN and provide its output via the CAN to the diagnostic connection.

This approach has a number of disadvantages. The time needed to bring the vehicle to the stable operating condition—sometimes up to 40 minutes or more—adds to the overall repair time for the vehicle. A faulty NOx sensor reading via the diagnostic connection of the vehicle's CAN may not be the result of a faulty NOx sensor because the NOx sensor reading via the diagnostic connection of the vehicle's CAN relies on a number of variables, such as the operation of the CAN and the operation of the other sensors coupled to the CAN. These disadvantages make testing of NOx sensors difficult and time-consuming, particularly in the repair facility setting where NOX sensors are tested via the CAN while installed on the vehicle.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one embodiment, a testing device is capable of testing a NOx sensor in an environment that does not have dew point detection capability. The testing device includes a connector configured to be coupled to the NOx sensor, an output indicator, and circuitry in communication with the connector and the output indicator. The circuitry is configured to send an unverified dew point signal to the NOx sensor via the connector and receive a sensor signal from the NOx sensor via the connector. The unverified dew point signal includes an indication that a temperature of the environment is at or above the dew point. The sensor signal includes an indication of operation of the NOx sensor in the environment. The circuitry is further configured to determine a status of the NOx sensor based on the received sensor signal and indicate, via the output indicator, the status of the NOx sensor.

In one example, the sensor signal includes an indication of NOx in the environment and the circuitry is configured to determine the status of the NOx sensor by determining whether the indication of the NOx is within a particular range. In another example, the particular range is a range of about −20.1 ppm to about 40.1 ppm of NOx in the environment. In another example, the circuitry is further configured to receive an indication of a type of NOx sensor before sending the unverified dew point signal to the NOx sensor. In another example, the circuitry is further configured to format the unverified dew point signal based on the type of NOx sensor before sending the unverified dew point signal to the NOx sensor.

In another example, the sensor signal includes an indication of an internal heater functionality of the NOx sensor and the circuitry is configured to determine the status of the NOx sensor based on the indication of the internal heater functionality of the NOx sensor. In another example, the sensor signal includes an indication of an output stability of the NOx sensor and the circuitry is configured to determine the status of the NOx sensor based on the indication of the output stability of the NOx sensor. In another example, the sensor signal includes an indication of a circuit check of the NOx sensor and the circuitry is configured to determine the status of the NOx sensor based on the indication of the circuit check of the NOx sensor. In another example, the sensor signal comprises an indication of $O_2$ in the environment, and the circuitry is configured to determine the status of the NOx sensor by determining whether the indication of the $O_2$ is within a particular range. In another example, the particular range of $O_2$ is a range of about 18.9% to about 21.1% of $O_2$ in the environment.

In another example, the output indicator includes one or more lights and the circuitry is configured to indicate the status of the NOx sensor by causing light of a particular color to be emitted from the one or more lights. In another example, the testing device further includes a housing configured to hold the circuitry and the output indicator and the connector is coupled to the housing or accessible through the housing. In another example, the housing has a volumetric capacity of less than or equal to about 20 cubic inches. In another example, the testing device further includes a printed circuit board that includes the circuitry and is located within the housing.

In another embodiment a method can be used to test a NOx sensor in an environment that does not have dew point detection capability. The method includes sending, by circuitry coupled to a connector, an unverified dew point signal to the NOx sensor via the connector and receiving, by the circuitry, a sensor signal from the NOx sensor via the connector. The unverified dew point signal indicates that a temperature of the environment is at or above the dew point. The sensor signal indicates an operation of the NOx sensor in the environment. The method further includes determining, by the circuitry, a status of the NOx sensor based on the received sensor signal and indicating, by an output indicator coupled to the circuitry, the status of the NOx sensor.

In one example, the sensor signal includes an indication of NOx in the environment and the circuitry determines the status of the NOx sensor by determining whether the indication of the NOx is within a particular range. In another example, the particular range is a range of about −20.1 ppm to about 40.1 ppm of NOx in the environment. In another example, the method further includes receiving, by the circuitry, an indication of a type of NOx sensor before sending the unverified dew point signal to the NOx sensor and formatting, by the circuitry, the unverified dew point signal based on the type of NOx sensor before sending the unverified dew point signal to the NOx sensor.

In another example, the sensor signal includes one or more sensor readings and the one or more sensor readings include one or more of: an indication of an internal heater functionality of the NOx sensor, an indication of an output stability of the NOx sensor, an indication of a circuit check of the NOx sensor, or an indication of $O_2$ in the environment. In another example, determining the status of the NOx sensor based on the received sensor signal includes determining, by the circuitry, the status of the NOx sensor based on the one or more sensor readings.

DESCRIPTION OF THE DRAWINGS

The foregoing aspects and many of the attendant advantages of the claimed subject matter will become more readily appreciated as the same become better understood by reference to the following detailed description, when taken in conjunction with the accompanying drawings, wherein:

DETAILED DESCRIPTION

The detailed description set forth below in connection with the appended drawings is intended as a description of various embodiments of the disclosed subject matter and is not intended to represent the only embodiments. Each embodiment described in this disclosure is provided merely as an example or illustration and should not be construed as preferred or advantageous over other embodiments. The illustrative examples provided herein are not intended to be exhaustive or to limit the invention to the precise forms disclosed. Similarly, any steps described herein may be interchangeable with other steps, or combinations of steps, in order to achieve the same or substantially similar result.

Embodiments of the present disclosure are directed to devices and methods of testing a NOx sensor in an environment that does not have dew point detection capability. In one embodiment, a testing device includes a connector configured to be coupled to the NOx sensor, an output indicator, and circuitry in communication with the connector and the output indicator. The circuitry is configured, for example, to send an unverified dew point signal to the NOx sensor via the connector and to receive a sensor reading from the NOx sensor. The sent unverified dew point signal includes an indication that a temperature of the environment is at or above the dew point and the received sensor reading includes an indication of NOx in the environment. The circuitry is further configured to determine a status of the NOx sensor based on the received sensor reading and to indicate, via the output indicator, the status of the NOx sensor.

The embodiments of devices and methods of testing a NOx sensor disclosed herein allow a NOx sensor to be tested without the vehicle being run to a stable operating state in order to test the NOx sensor. Sending the unverified dew point signal to the NOx sensor allows the NOx sensor to begin testing under conditions that do not require sensors to determine whether the temperature of the environment is below the dew point. In certain scenarios, an operator of the devices and/or methods disclosed herein will be able to ascertain whether the environment is at or above a dew point (e.g., whether it is not raining in the testing environment, whether dew is forming on surfaces of the testing environment, etc.). This alleviates any need to run a vehicle to get to a stable operating condition below the dew point merely to test a NOx sensor. It also allows the NOx sensor to be tested without using the CAN on the vehicle, thereby reducing the number of variables involved in NOx sensor testing. Other benefits of the embodiments disclosed herein will be apparent from the description below and the attached drawings.

In the following description, numerous specific details are set forth in order to provide a thorough understanding of exemplary embodiments of the present disclosure. It will be apparent to one skilled in the art, however, that many embodiments of the present disclosure may be practiced without some or all of the specific details. In some instances, well known aspects have not been described in detail in order to not unnecessarily obscure various aspects of the present disclosure. Further, it will be appreciated that embodiments of the present disclosure may employ any combination of features described herein.

Figure 1:
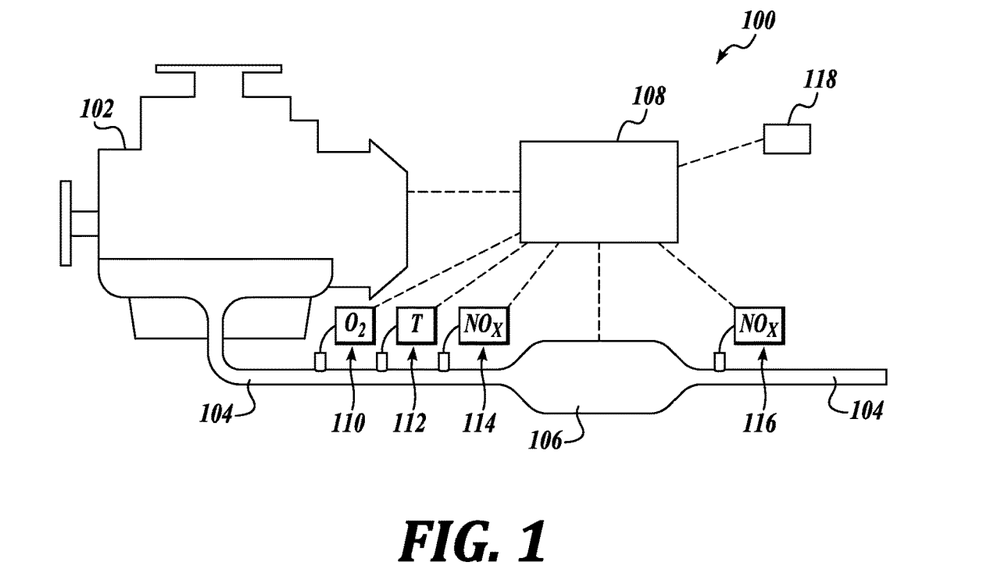
FIG. 1 depicts an embodiment of an environment in which systems and methods of the present disclosure are employed.

Depicted in FIG. 1 is an embodiment of a power generation and exhaust system 100. The system 100 includes a fuel burning engine 102 and an exhaust pipe, shown as a vehicle tailpipe 104, configured to carry exhaust from the engine 102. An engine aftertreatment system (EAS) 106 is located along the tailpipe 104. The EAS 106 is configured to treat the exhaust passing through the tailpipe 104 before it is released into the atmosphere. In some embodiments, the EAS 106 is configured to convert pollutant compounds in the diesel exhaust into non-pollutant compounds and/or filter pollutant compounds from the diesel exhaust. The system 100 also includes a number of sensors that sense the operation of the system and associated environment. The sensors, as well as components of the system 100, are communicatively coupled via a CAN 108. In some embodiments, the CAN 108 is configured to communicate sensor signals from and to sensors in the system 100 and to control components in the system 100.

In the particular embodiment depicted in FIG. 1, the system 100 includes the following sensors: an oxygen sensor 110 configured to generate an oxygen sensor signal indicative of a level of oxygen in the tailpipe 104 between the engine 102 and the EAS 106, a temperature sensor 112 configured to generate a temperature sensor signal indicative of temperature in the tailpipe 104 between the engine 102 and the EAS 106, a NOx sensor 114 configured to generate a NOx sensor signal indicative of a level of NOx in the tailpipe 104 between the engine 102 and the EAS 106, and a NOX sensor 116 configured to generate a NOx sensor signal indicative of a level of NOx in the tailpipe 104 after the EAS 106. In other embodiments, the system 100 includes other sensors, such as an oxygen sensor located on the tailpipe 104 after the EAS 106, a temperature sensor located on the tailpipe 104 after the EAS 106, one or more sensors in the engine 102 configured to monitor performance of the engine 102 (e.g., a temperature sensor in the engine 102), one or more sensors in the EAS 106 configured to monitor performance of the EAS 106, or any other sensor. In some embodiments, the CAN 108 receives temperature signals from a temperature sensor in the engine 102 instead of or in addition to the temperature signals from the temperature sensor 112. In some embodiments, the CAN 108 is configured to send verified dew point signals to one or more sensors in the system 100, where the activation signals are based on measured conditions within the system 100. In one example, the CAN 108 receives temperature and/or humidity signals from sensors in the system 100 and sends a verified dew point signal based on the ambient temperature and/or humidity within the system 100.

Figure 2:
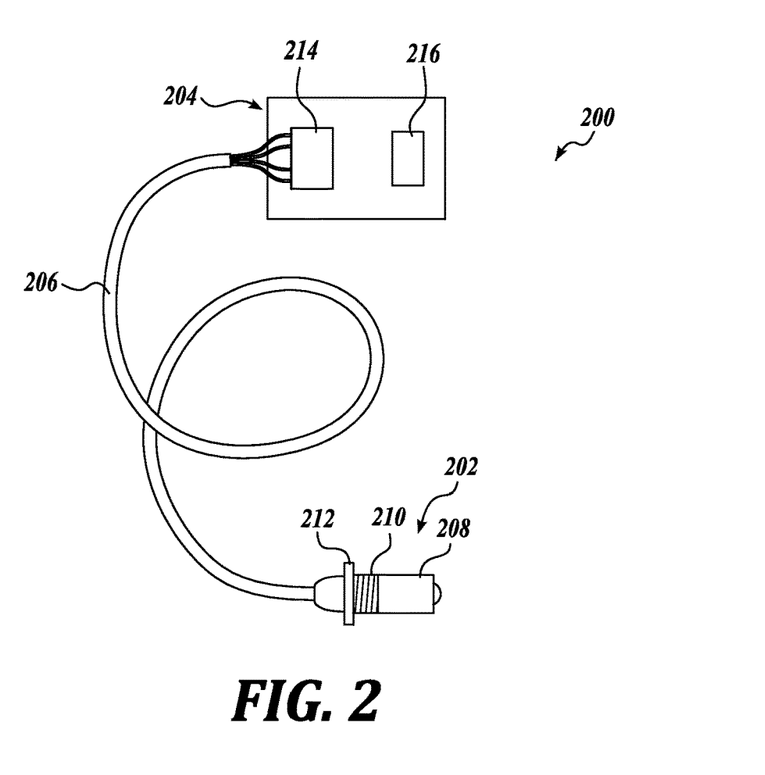
FIG. 2 depicts an example of a plug sensor usable in the system depicted in FIG. 1 or in any other system, in accordance with embodiments disclosed herein.

Depicted in FIG. 2 is an example of a plug sensor 200 usable in the system 100 depicted in FIG. 1 or in any other system. In some embodiments, the plug sensor 200 is an oxygen sensor (e.g., oxygen sensor 110), a temperature sensor (e.g., temperature sensor 112), a NOx sensor (e.g., NOx sensor 114 or NOx sensor 116), another type of sensor, or any combination of sensors. As shown in FIG. 2, the plug sensor 200 includes a sensor portion 202 and a controller 204. The sensor portion 202 and the controller 204 are communicatively coupled by a cable 206. The cable 206 includes one or more electrical wires configured to convey signals between the sensor portion 202 and a controller 204.

In some embodiments, the sensor portion 202 includes a sensor end 208, a threaded portion 210, and a stop member 212. The sensor end 208 is configured to be inserted through a hole in a barrier (e.g., through a hole in the wall of the tailpipe 104). The threaded portion 210 is configured to interact with a threaded portion of the hole to secure the sensor portion 202 to the barrier (e.g., the wall of the tailpipe 104) with the sensor end 208 located in an environment within the barrier (e.g., the environment within the tailpipe 104). The stop member 212 is configured to be in physical contact with the barrier when the threaded portion 210 interacts with the threaded portion of the hole to secure the sensor portion 202 to the barrier. In some embodiments, the threaded portion 210 or the stop member 212 includes a sealing mechanism (e.g., an o-ring, a thread sealant, a sealing washer, etc.) configured to seal the hole through which the sensor portion 202 is inserted.

As described briefly above, signals from the sensor portion 202 are conveyed via cables 206 to the controller 204. In this regard, the controller 204 in one embodiment includes a first connector 214 configured to be coupled to the one or more electrical wires of the cable 206. In one embodiment, the first connector 214 is configured to be fixedly attached to the one or more electrical wires of the cable 206, such as the one or more electrical wires of the cable 206 being soldered or bonded to the first connector 214. The controller 204 also includes a second connector 216 configured to be coupled to a CAN, such as, e.g., the CAN 108. In one embodiment, the second connector 216 is configured to be removably coupled to a cable coupled to the CAN, such as via a connector on an end of the cable that mates with the second connector 216 and is capable of being removed from the second connector 216 by hand.

In some embodiments, the controller 204 is configured to process signals received from the sensor portion 202 via the first connector 214, and to send signals to the CAN via the second connector 216. In one example, the controller 204 is configured to receive analog signals from the sensor portion 202 via the first connector 214, to convert the analog signals to digital signals, and to send the digital signals to the CAN via the second connector 216. In another example, the controller 204 is configured to receive a signal from the sensor portion 202 via the first connector 214, to determine a status code (e.g., an error code) based on the signal received from the signal from the sensor portion 202, and to send the status code to the CAN via the second connector 216. In other examples, the controller 204 is configured to receive any other signal from the sensor portion 202 via the first connector 214, to convert the received signal to a new signal and/or generate a new signal from the received signal, and to send the new signal to the CAN via the second connector 216.

In some embodiments, the controller 204 is configured to process signals received from the CAN via the second connector 216 to send signals to the sensor portion 202 via the first connector 214. In one example, the controller 204 is configured to receive signals from the CAN via the second connector 216, to determine a new signal to send to the sensor portion 202 (e.g., an activation signal), and to send the new signal to the sensor portion 202 via the first connector 214. In another example, the controller 204 is configured to convert the digital activation signal into an analog activation signal, and to send the analog activation signal to the sensor portion 202 via the first connector 214. In other examples, the controller 204 is configured to receive any other signal from the CAN via the second connector 216, to convert the received signal to a new signal and/or generate a new signal from the received signal, and to send the new signal to the sensor portion 202 via the first connector 214.

Referring back to FIG. 1, in one embodiment, sensor signals from any of the sensors in the system 100 (e.g., oxygen sensor 110, temperature sensor 112, NOx sensor 114, or NOX sensor 116) are broadcast via the CAN 108. Such sensor signals broadcast via the CAN 108 are available to be read by any of the other sensors or components communicatively coupled to the CAN 108. In this way, the CAN 108 operates as a communications bus for sensor signals. In one example, an oxygen sensor signal broadcast from the oxygen sensor 110 may be read by the engine 102 or the EAS 106. In another example, a temperature sensor signal broadcast from the temperature sensor 112 may be read by the NOx sensor 114 or the NOx sensor 116. In another embodiment, the CAN 108 is configured to send control signals to one or more components of the system 100 (e.g., the engine 102 or the EAS 106) based on sensor signals received from one or more of the components. In one example, the CAN 108 receives temperature sensor signals from the temperature sensor 112 and NOx senor signals from the NOx sensor 114 and the CAN 108 sends a control signal to the EAS 106 based on the received temperature sensor signals and NOx senor signals.

In the embodiment depicted in FIG. 1, a diagnostic connection 118 is provided, which is communicatively coupled to the CAN 108. The diagnostic connection 118 is configured to permit a device external to the system 100, such as a diagnostic testing device, to be coupled to the CAN 108 to read information from the CAN 108. In one example, a diagnostic testing device coupled to the CAN 108 via the diagnostic connection 118 is capable of reading sensor signals broadcast on the CAN 108 by one or more of the sensors in the CAN system 100. In another example, a diagnostic testing device coupled to the CAN 108 via the diagnostic connection 118 is capable of reading control signals sent from the CAN 108 to one or more of a sensor in the CAN system 100 or a component in the system 100. In another example, a diagnostic testing device coupled to the CAN 108 via the diagnostic connection 118 is capable of reading diagnostic codes generated or transmitted by the CAN 108.

In one particular example, the diagnostic connection 118 can be used to determine an operating status of the NOx sensor 114. For example, a vehicle that includes the system 100 is operated (e.g., the engine 102 is run) for a time until the vehicle achieves a stable operating condition. The temperature sensor 112 broadcasts, via the CAN 108, temperature signals indicative of the temperature inside the tailpipe 104. The NOx sensor 114 receives, via the CAN 108, the temperature signals sent by the temperature sensor 112. When the temperature signals from the temperature sensor 112 indicate that the temperature in the tail pipe is above a dew point, the NOx sensor 114 activates and begins to generate NOx sensor signals indicative of NOx in the tail pipe 104. The NOx sensor 114 does not activate until the temperature in the tail pipe is above a dew point because activating the NOx sensor 114 in the presence of liquid water may damage the NOx sensor 114. The NOx sensor 114 broadcasts the NOx sensor signals indicative of NOx in the tail pipe 104 via the CAN 108. A diagnostic testing device coupled to the CAN 108 via the diagnostic connection 118 is capable of reading the NOx sensor signals sent by the NOx sensor 114 and determining an operating status of the NOx sensor 114 based on the NOx sensor signals.

While the diagnostic connection 118 can be used to determine an operating status of the NOx sensor 114, there are several drawbacks to testing the NOx sensor 114 using the diagnostic connection. In one example, the time needed to bring the vehicle to the stable operating condition adds to the overall time required to test the NOx sensor 114. In some cases, the engine 102 is operated for up to 40 minutes or more in order to achieve the stable operating condition. In another example, a NOx sensor signals indicating that the NOx sensor 114 is faulty may not be the result of the NOx sensor 114 being faulty. In some cases, obtaining a proper NOx sensor signal requires proper operation of several portions of the system 100, such as proper operation of the CAN 108, proper operation of the temperature sensor 112, and proper operation of any other sensor or component of the system 100.

Figure 3:
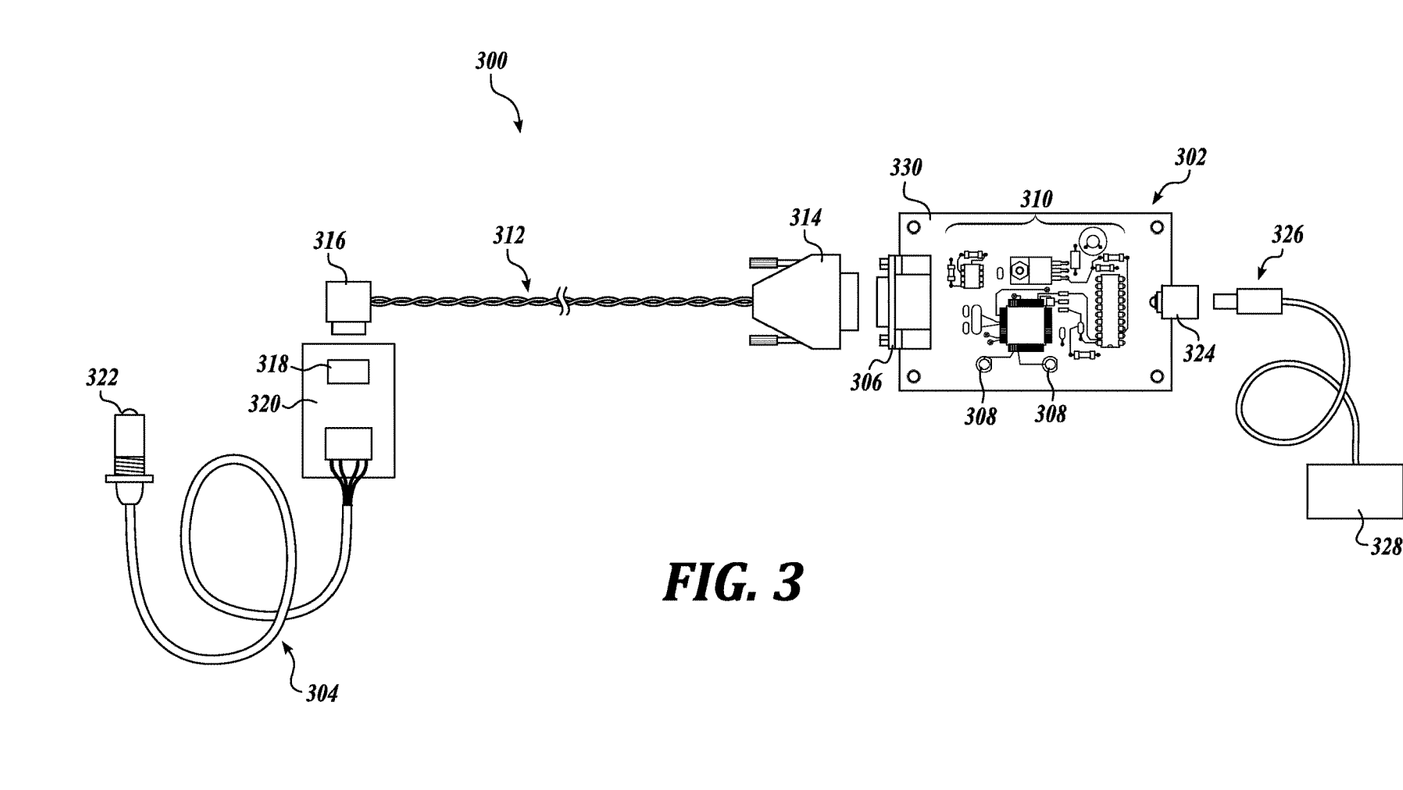
FIG. 3 depicts an embodiment of a system with a testing device for testing a NOx sensor, in accordance with embodiments disclosed herein.

An embodiment of a system 300 with a testing device 302 for testing a NOx sensor 304 is depicted in FIG. 3. The testing device 302 includes a connector 306, an output indicator 308, and circuitry 310. The circuitry 310 is in communication with the connector 306 and the output indicator 308. In some embodiments, the testing device 302 is capable of testing the NOx sensor 304 in an environment that does not have dew point detection capability. This allows the testing device 302 to test the NOx sensor 304 when the NOx sensor 304 is not coupled to a CAN (e.g., CAN 108) that sends dew point activation signals based on dew point detection capabilities. This also allows the testing device 302 to test the NOx sensor 304 when the NOx sensor 304 is either installed on a tailpipe or when the NOx sensor 304 is not installed on a tailpipe. Additionally, because the testing device 302 is capable of testing the NOx sensor 304 in an environment that does not have dew point detection, the NOx sensor 304 does not need to be connected to a tailpipe in a vehicle operating at a stable operating condition to be tested. This alleviates the time required to bring the vehicle to the stable operating condition in order to test the NOx sensor 304. The testing device 302 is also capable of testing the NOx sensor 304 without the testing device 302 being connected to a CAN on a vehicle.

The connector 306 is configured to be coupled to the NOx sensor 304. In the particular embodiment shown in FIG. 3, the connector 306 is configured to be coupled to the NOx sensor 304 via a cable 312. The cable 312 includes a first connector 314 and a second connector 316. The first connector 314 is configured to mate with the connector 306 of the testing device 302. The second connector 316 is configured to mate with a CAN connector 318 on a controller 320 of the NOx sensor 304. The NOx sensor 304 also includes a sensor portion 322 communicatively coupled to the controller 320.

The circuitry 310 is configured to send one or more signals to the NOx sensor 304 via the connector 306 to activate the NOx sensor 304. In one embodiment, the circuitry 310 is configured to send an unverified dew point signal to the NOx sensor 304 via the connector 306, where the unverified dew point signal includes an indication that a temperature of the environment is at or above the dew point. The unverified dew point signal is unverified because the circuitry 310 does not receive readings of actual conditions in the environment about the dew point (e.g., temperature sensor readings, humidity sensor readings, etc.) when the circuitry 310 sends the unverified dew point signal. Because the circuitry 310 is configured to send an unverified dew point signal, the circuitry 310 can be used without being coupled to dew point detection equipment. In other words, the testing device 302 is able to send the unverified dew point signal to the NOx sensor 304 without receiving any signals indicative of the actual temperature or dew point in the environment. In some embodiments, the indication, unverified dew point signal, that a temperature of the environment is at or above the dew point is a binary indication (e.g., a "1" indicating that the temperature of the environment is at or above the dew point or a "0" indicating that the temperature of the environment below the dew point). To protect the NOx sensor 304 during the test, a technician may ensure that the NOx sensor 304 is located in a testing system where exposure to condensation or other liquid is unlikely during the test before initiating the circuitry 310.

In one example, the unverified dew point signal is formatted in a way that a temperature sensor would send a temperature sensor signal indicative of a temperature of an environment via a CAN (e.g., the temperature sensor 112 would send a temperature sensor signal indicative of the environment inside tailpipe 104 or a temperature sensor in the engine 102 would send an indication of engine temperature via the CAN 108). In this way, the NOx sensor 304 receives an unverified dew point signal which appears as an actual temperature sensor signal. In one example, the unverified dew point signal is formatted in a way that a CAN (e.g., CAN 108) would format a verified dew point signal when the vehicle is operating. In any embodiment, the unverified dew point signal indicates that the temperature of the environment is at or above the dew point so that the NOx sensor 304 will activate even though the NOx sensor 304 is in an environment that does not have dew point detection capabilities. To protect the NOx sensor 304 during the test, a technician may ensure that the NOx sensor 304 is located in a testing environment where exposure to condensation or other liquid is unlikely during the test.

In some embodiments, the circuitry 310 is configured to send other signals to the NOx sensor 304 to activate the NOx sensor 304 or to keep the NOx sensor 304 activated. In one example, the circuitry 310 is configured to send internal heater activation signals to the NOx sensor 304 to activate an internal heater of the sensor end 322 of the NOx sensor 304. In one embodiment, the circuitry 310 sends internal heater activation signal to the NOx sensor 304 at predetermined intervals (e.g., every 100 milliseconds) such that the internal heater of the NOx sensor 304 arrives at a stable condition within a particular amount of time, such as within two minutes. In this case, where the internal heater of the NOx sensor 304 arrives at a stable condition within two minutes, the time for the NOx sensor 304 to be ready for providing a sensor reading is significantly less than the time to bring the vehicle up to a stable operating condition (e.g., up to 40 minutes or more).

The circuitry 310 is further configured to receive a sensor signal from the NOx sensor 304 via the connector 306. The sensor signal includes an indication of the operation of the NOx sensor 304 in the environment. In some embodiments, the sensor signal is formatted by the NOx sensor 304 for sending via a CAN before the sensor signal is sent to the connector 306. In these embodiments, the circuitry 310 is configured to decode the CAN-formatted sensor signal received via the connector 306.

In one embodiment, the operation of the NOx sensor 304 is a measurement of NOx and the sensor signal includes an indication of NOx in the environment. In another embodiment, the operation of the NOx sensor 304 is a measurement of $O_2$ and the sensor signal includes an indication of $O_2$ in the environment. In another embodiment, the operation of the NOx sensor 304 is testing functionality of an internal heater of the NOx sensor 304 and the sensor signal includes an indication of internal heater functionality of the NOx sensor 304 in the environment. In another embodiment, the operation of the NOx sensor 304 is testing output stability of the NOx sensor 304 and the sensor signal includes an indication of output stability of the NOx sensor 304 in the environment. In another embodiment, the operation of the NOx sensor 304 is performing a circuit check of the NOx sensor 304 and the sensor signal includes an indication of circuit check of the NOx sensor 304 in the environment. In other embodiments, the operation of the NOx sensor 304 includes any other operation of the NOx sensor 304 in the environment.

The circuitry 310 is further configured to determine a status of the NOx sensor 304 based on the received sensor signal. In various embodiments, the circuitry 310 is configured to determine the status of the NOx sensor 304 based on a reading or any combination of sensor readings in the received sensor signal. In one embodiment, where the sensor signal includes an indication of NOx in the environment, the circuitry is configured to determine the status of the NOx sensor by determining whether the indication of the NOx in the environment is within a particular range. In one example, the particular range is a range of about −20.1 ppm to about 40.1 ppm of NOx in the environment, where "about" means within 5 ppm of the target value. If the indication of the NOx in the environment is inside the range, then the status of the NOx sensor 304 is determined to be operating properly; otherwise, the status of the NOx sensor 304 is determined to be not operating properly.

In another embodiment, where the sensor signal includes an indication of $O_2$ in the environment, the circuitry is configured to determine the status of the NOx sensor by determining whether the indication of the $O_2$ is within a particular range. In one example, the particular range is a range of about 18.9% to about 21.1% of $O_2$ in the environment, where "about" means within 0.2% of the target value. If the indication of the $O_2$ in the environment is inside the range, then the status of the NOx sensor 304 is determined to be operating properly; otherwise, the status of the NOx sensor 304 is determined to be not operating properly.

In other embodiments, the sensor signal includes an indication of a "pass" or a "fail" for one or more of the following sensor readings: internal heater functionality of the NOx sensor 304, output stability of the NOx sensor 304, circuit check of the NOx sensor 304, power status of the NOx sensor 304, or temperature status of the NOx sensor 304. If the sensor signal includes a "pass" indication for each of the one or more sensor readings, then the status of the NOx sensor 304 is determined to be operating properly; otherwise, the status of the NOx sensor 304 is determined to be not operating properly.

In another embodiment, the circuitry 310 is further configured to determine a status of the NOx sensor 304 based on a number of sensor readings in the received sensor signal. In one example, the sensor signal includes indications of a power status of the NOx sensor 304, a temperature status of the NOx sensor 304, a stability of a NOx reading of the NOx sensor 304, a stability of an $O_2$ reading of the NOx sensor 304, an internal heater functionality of the NOx sensor 304, a NOx reading of the NOx sensor 304, and an $O_2$ reading of the NOx sensor 304. If the sensor signal includes a "pass" indication for each of the power status, the temperature status, the stability of a NOx reading, the stability of an $O_2$ reading, and the internal heater functionality, and the sensor signal includes a NOx reading of and an $O_2$ reading within particular ranges, then the status of the NOx sensor 304 is determined to be operating properly. If any one of those sensor readings is either a "fail" or outside of the particular ranges, then the NOx sensor 304 is determined to be not operating properly.

The circuitry 310 is further configured to indicate, via the output indicator 308, the status of the NOx sensor 304. In the embodiment shown in FIG. 3, the output indicator 308 includes two light emitting diodes (LEDs) of different colors, where one color indicates that the NOx sensor 304 is determined to be operating properly and the other color indicates that the NOx sensor 304 is determined to be not operating properly. In another embodiment, the output indicator 308 is a single light (e.g., a single LED) that is illuminated in a first pattern (e.g., illuminated without pulsing) to indicate that the NOx sensor 304 is determined to be operating properly and in a second pattern (e.g., illuminated in a pulsing manner) to indicate that the NOx sensor 304 is determined to be not operating properly. In another embodiment, the output indicator 308 is a display capable of displaying a first set of alphanumeric characters (e.g., "PASS") to indicate that the NOx sensor 304 is determined to be operating properly and a second set of alphanumeric characters (e.g., "FAIL") to indicate that the NOx sensor 304 is determined to be not operating properly. In another embodiment, the output indicator 308 is an audio indicator (e.g., speaker) configured to make a first noise to indicate that the NOx sensor 304 is determined to be operating properly and a second noise to indicate that the NOx sensor 304 is determined to be not operating properly. The output indicator 308 can take any number of other forms or variations on the examples described herein in order to indicate the status of the NOx sensor 304.

The circuitry 310 includes one or more hardware components configured to perform any of the functions described herein. The one or more hardware components include one or more of microprocessors, transistors, resistors, diodes, amplifiers, and the like. In some examples, at least one hardware component of the circuitry 310 (e.g., a microprocessor) is programmed with software that, when executed by the one or more hardware components of the circuitry 310, causes the circuitry 310 to perform any of the functions described herein.

In the embodiment shown in FIG. 3, the testing device 302 includes a power connector 324 configured to be removably coupled to a power cord 326 that is coupled to a power source 328. In some embodiments, the circuitry 310 is configured to begin testing of the NOx sensor 304 in response to the testing device 302 being coupled to both the power source 328 and the NOx sensor 304. In alternative embodiments, the testing device includes a power source (e.g., rechargeable battery) to power the testing device. In some embodiments, the testing device is configured to provide electrical power to the NOx sensor 304 via the cord 312.

In the embodiment shown in FIG. 3, the testing device 302 includes a printed circuit board 330. The printed circuit board 330 includes the circuitry 310. In some embodiments, including the embodiment shown in FIG. 3, the circuit board 330 also includes the connector 306, the output indicator 308, and the power connector 324.

In some embodiments, the circuitry 310 is configured to decode CAN-formatted messages received from the NOx sensor 304 and to encode signals in a CAN format to send the signals to the NOx sensor 304. In some embodiments, multiple different types of NOx sensors, which use a different type of signal formatting, are capable of being connected to the testing device 302. For example, in some embodiments, NOx sensors placed between an engine and an EAS (e.g., NOx sensor 114 in FIG. 1) are one type of NOx sensor and NOx sensors placed after an EAS (e.g., NOx sensor 116 in FIG. 1) are a different type of NOx sensor. In some embodiments, the circuitry 310 is configured to receive an indication of the type of NOx sensor from the NOx sensor 304 before sending any signal to the NOx sensor 304 and to format the signals sent to the NOx sensor 304 based on the type of NOx sensor before sending any signal to the NOx sensor 304. For example, the circuitry 310 receives an indication of the type of NOx sensor before sending the unverified dew point signal to the NOx sensor 304 and to format the unverified dew point signal based on the type of NOx sensor before sending the unverified dew point signal to the NOx sensor 304.

Figure 4:
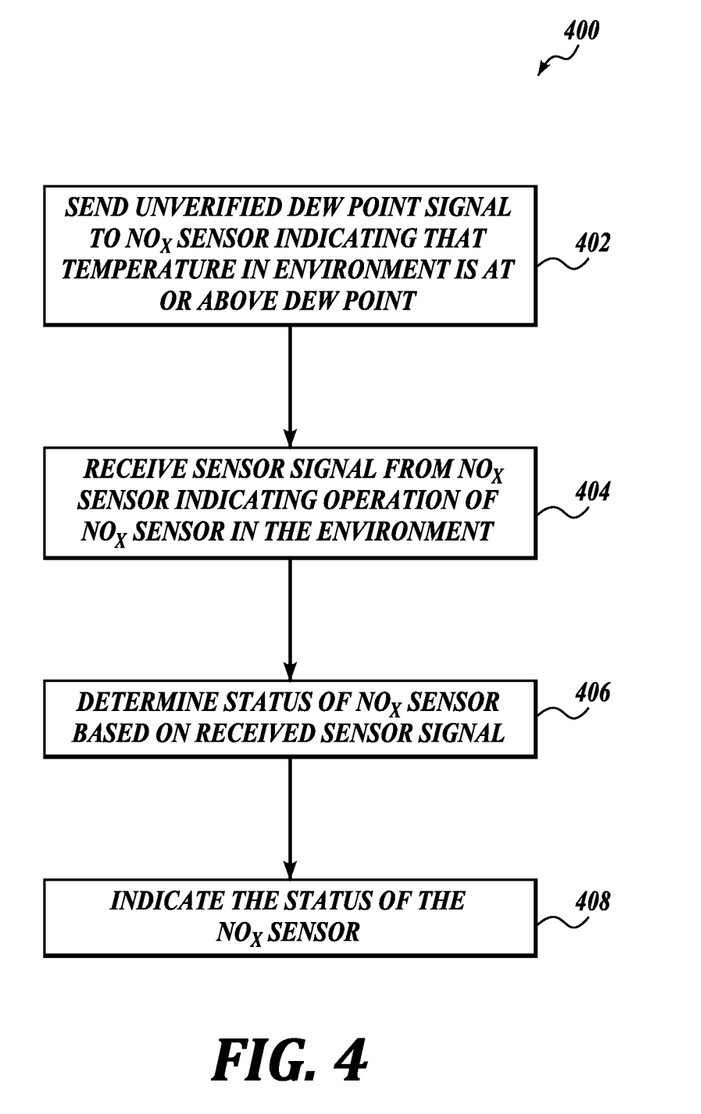
FIG. 4 depicts an embodiment of a method of testing a NOx sensor in an environment that does not have dew point detection capability using a testing device, in accordance with embodiments disclosed herein.

An embodiment of a method 400 of testing a NOx sensor in an environment that does not have dew point detection using any of the testing devices described herein is depicted in FIG. 4. At block 402, an unverified dew point signal is sent, by circuitry coupled to a connector, to the NOx sensor via the connector. In one embodiment, the unverified dew point signal indicating that a temperature of the environment is at or above the dew point.

At block 404, a sensor signal is received, by the circuitry, from the NOx sensor via the connector. In one embodiment, the sensor signal includes an indication of operation of the NOx sensor in the environment. In one embodiment, the sensor signal includes an indication of NOx in the environment. In another embodiment, the sensor signal include one or more sensor readings and the one or more sensor readings include one or more of: an indication of an internal heater functionality of the NOx sensor, an indication of an output stability of the NOx sensor, an indication of a circuit check of the NOx sensor, or an indication of $O_2$ in the environment.

At block 406, a status of the NOx sensor is determined by the circuitry based on the received sensor signal. In one embodiment, the circuitry determines the status of the NOx sensor based on the received sensor signal by determining whether the indication of the NOx is within a particular range. In one example, the particular range is a range of about −20.1 ppm to about 40.1 ppm of NOx in the environment. In one embodiment, the circuitry determines the status of the NOx sensor based on determining the status of the NOx sensor based on the one or more sensor readings.

At block 408, the status of the NOx sensor is indicated by an output indicator coupled to the circuitry. In some embodiments, the output indicator includes one or more lights. In some embodiments, the circuitry is configured to indicate the status of the NOx sensor by causing light of a particular color to be emitted from the one or more lights. In some embodiments, the output indicator is an audio indicator configured to make a particular sound.

In other embodiments, the method 400 includes steps not shown in FIG. 4. In one example, the method 400 also includes the circuitry receiving an indication of a type of NOx sensor before sending the unverified dew point signal to the NOx sensor. In another example, the method 400 also includes the circuitry formatting the unverified dew point signal based on the type of NOx sensor before sending the unverified dew point signal to the NOx sensor.

Figure 5A:
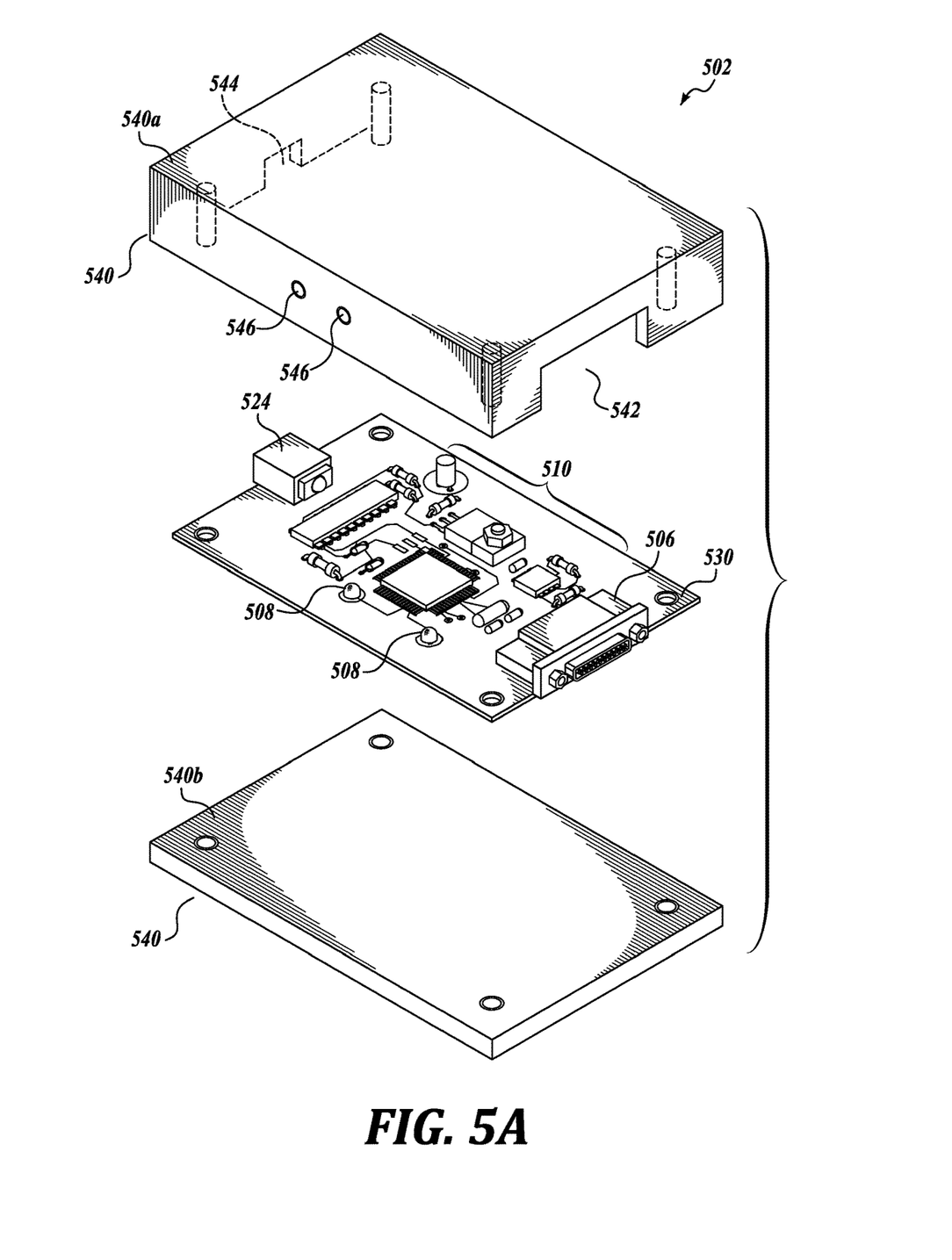
FIGS. 5A and 5B are exploded and assembled views, respectively, of an embodiment of a testing device, in accordance with embodiments disclosed herein.
Figure 5B:
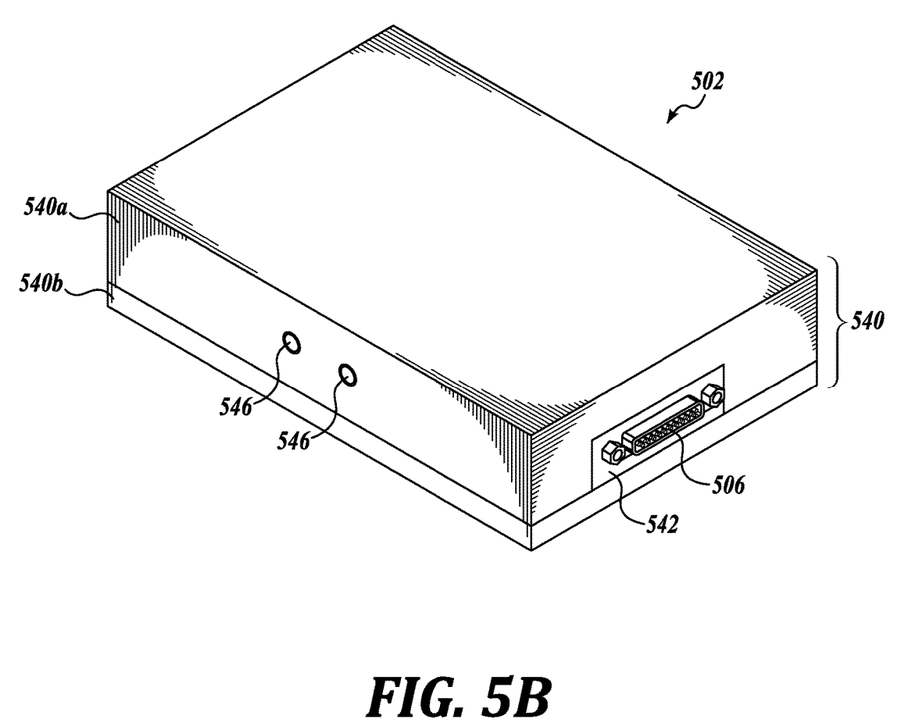

Depicted in FIGS. 5A and 5B are exploded and assembled views, respectively, of an embodiment of a testing device 502. The testing device includes a printed circuit board 530 that includes a connector 506, an output indicator 508, circuitry 510, and power connector 524. The connector 506, the output indicator 508, and the circuitry 510 are capable of performing the functions described herein with respect to other embodiments of connectors, output indicators, and circuitry (e.g., connector 306, output indicator 308, and circuitry 310).

The testing device 502 also includes a housing 540. As shown in the embodiment depicted in FIG. 5B, the printed circuit board is configured to be located in the housing 540. In the particular embodiment shown in FIGS. 5A and 5B, the housing 540 includes an upper housing 540a and a lower housing 540b; however, the housing 540 may take any other form. The housing 540 includes openings 542, 544, and 546 in the upper housing. The openings 542, 544, and 546 make, respectively, the connector 506, the power connector 524, and the output indicator 508 accessible through the housing 540. In some embodiments, the housing has a volumetric capacity of less than or equal to about 20 cubic inches. Such a volumetric capacity generally provides the housing 540 with a size that makes the testing device 502 a handheld device. Having a handheld testing device 502 increases the ease of use for technicians and others to reduce the amount of time to test a NOx sensor.

Figure 6:
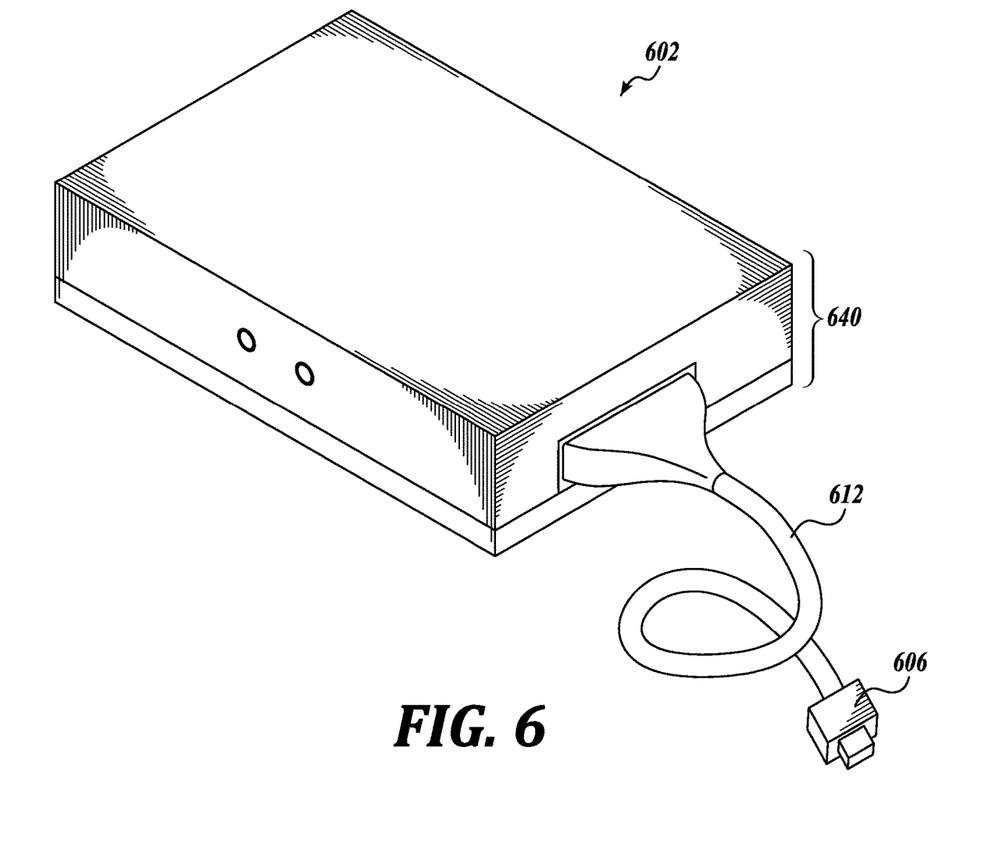
FIG. 6 depicts another embodiment of a testing device with a housing, in accordance with embodiments disclosed herein.

Another embodiment of a testing device 602 with a housing 640 is depicted in FIG. 6. The testing device 602 includes a connector 606 that is coupled to the housing 640 via a cable 612. The connector 606 is capable of performing the functions described herein with respect to other embodiments of connectors (e.g., connector 306). In this embodiment, a separate cable may not be required to couple the testing device 602 to a NOx sensor because the connector 606 can be directly coupled to the NOx sensor. The testing device also includes other components not visible through the housing 640, such as an output indicator and circuitry, which are capable of performing the functions described herein with respect to other embodiments of output indicators and circuitry (e.g., output indicator 308 and circuitry 310).

A number of embodiments depicted herein have been described in the context of a vehicle engine. However, the embodiments described herein are not limited to NOx sensors used in conjunction with vehicle engines. The embodiments described herein may be used to test NOx sensors used with any other type of engine, such as diesel generators, diesel-powered pumps, and the like.

The principles, representative embodiments, and modes of operation of the present disclosure have been described in the foregoing description. However, aspects of the present disclosure which are intended to be protected are not to be construed as limited to the particular embodiments disclosed. Further, the embodiments described herein are to be regarded as illustrative rather than restrictive. It will be appreciated that variations and changes may be made by others, and equivalents employed, without departing from the spirit of the present disclosure. Accordingly, it is expressly intended that all such variations, changes, and equivalents fall within the spirit and scope of the present disclosure, as claimed.

The invention claimed is:

1. A testing device for testing a NOx sensor in an environment having a temperature below the dew point, wherein the NOx sensor is disconnected from a system having a controller configured to output one or more verified dew point signals to the NOx sensor indicative of at least one of measured temperature and humidity conditions within the system, the testing device comprising:
   a connector configured to be coupled to the NOx sensor;
   an output indicator; and
   circuitry in communication with the connector and the output indicator, wherein the circuitry is configured to:
      send a first signal to the NOx sensor via the connector indicating that a temperature of the environment is at or above the dew point in order to activate the NOx sensor,
      receive a second signal from the NOx sensor via the connector indicating the operation of the NOx sensor in the environment,
      determine a status of the NOx sensor based on the received second signal, and
      indicate, via the output indicator, the status of the NOx sensor.

2. The testing device of claim 1, wherein the second signal comprises an indication of NOx in the environment, and wherein the circuitry is configured to determine the status of the NOx sensor by determining whether the indication of the NOx is within a particular range.

3. The testing device of claim 2, wherein the particular range of NOx in the environment, as measured by the NOx sensor, is a range of about −20.1 ppm to about 40.1 ppm.

4. The testing device of claim 1, wherein the circuitry is further configured to:
   receive an indication of a type of NOx sensor before sending the first signal to the NOx sensor.

5. The testing device of claim 4, wherein the circuitry is further configured to:
   format the first signal based on the type of NOx sensor before sending the first signal to the NOx sensor.

6. The testing device of claim 1, wherein the second signal comprises an indication of an internal heater functionality of the NOx sensor, and wherein the circuitry is configured to determine the status of the NOx sensor based on the indication of the internal heater functionality of the NOx sensor.

7. The testing device of claim 1, wherein the second signal comprises an indication of an output stability of the NOx sensor, and wherein the circuitry is configured to determine the status of the NOx sensor based on the indication of the output stability of the NOx sensor.

8. The testing device of claim 1, wherein the second signal comprises an indication of a circuit check of the NOx sensor, and wherein the circuitry is configured to determine the status of the NOx sensor based on the indication of the circuit check of the NOx sensor.

9. The testing device of claim 1, wherein the second signal comprises an indication of $O_2$ in the environment, and wherein the circuitry is configured to determine the status of the NOx sensor by determining whether the indication of the $O_2$ is within a particular range.

10. The testing device of claim 9, wherein the particular range of $O_2$ is a range of about 18.9% to about 21.1% of $O_2$ in the environment.

11. The testing device of claim 1, wherein the output indicator includes one or more lights, and wherein the circuitry is configured to indicate the status of the NOx sensor by causing light of a particular color to be emitted from the one or more lights.

12. The testing device of claim 1, further comprising:
   a housing configured to hold the circuitry and the output indicator, wherein the connector is coupled to the housing or accessible through the housing.

13. The testing device of claim 12, wherein the housing has a volumetric capacity of less than or equal to about 20 cubic inches.

14. The testing device of claim 12, further comprising:
   a printed circuit board including the circuitry;
   wherein the printed circuit board is located within the housing.

15. A method of testing a NOx sensor in an environment having a temperature below the dew point wherein the NOx sensor is disconnected from a system having a controller configured to output one or more verified dew point signals to the NOx sensor indicative of at least one of measured temperature and humidity conditions within the system, the method comprising:
   sending, by circuitry coupled to a connector, a first signal to the NOx sensor via the connector indicating that a temperature of the environment is at or above the dew point in order to activate the NOx sensor;
   receiving, by the circuitry, a second signal from the NOx sensor via the connector indicating the operation of the NOx sensor in the environment;
   determining, by the circuitry, a status of the NOx sensor based on the received second signal; and
   indicating, by an output indicator coupled to the circuitry, the status of the NOx sensor.

16. The method of claim 15, wherein the second signal comprises an indication of NOx in the environment, and wherein determining the status of the NOx sensor based on the received second signal comprises determining whether the indication of the NOx is within a particular range.

17. The method of claim 16, wherein the particular range of NOx in the environment, as measured by the NOx sensor, is a range of about −20.1 ppm to about 40.1 ppm.

18. The method of claim 15, further comprising:
   receiving, by the circuitry, an indication of a type of NOx sensor before sending the first signal to the NOx sensor; and
   formatting, by the circuitry, the first signal based on the type of NOx sensor before sending the first signal to the NOx sensor.

19. The method of claim 15, wherein the second signal comprises one or more sensor readings, wherein the one or more sensor readings include one or more of: an indication of an internal heater functionality of the NOx sensor, an indication of an output stability of the NOx sensor, an indication of a circuit check of the NOx sensor, or an indication of $O_2$ in the environment.

20. The method of claim 19, wherein determining the status of the NOx sensor based on the received second signal includes determining, by the circuitry, the status of the NOx sensor based on the one or more sensor readings.

* * * * *